United States Patent
Teng et al.

(10) Patent No.: US 12,054,612 B2
(45) Date of Patent: Aug. 6, 2024

(54) BIOPRINTABLE MATERIAL AND METHOD FOR FABRICATING THE SAME

(71) Applicant: Industrial Technology Research Institute, Hsinchu (TW)

(72) Inventors: Yun-Chung Teng, Kaohsiung (TW); Jen-Huang Huang, Hsinchu (TW); Ying-Wen Shen, Zhunan Township (TW); Yu-Bing Liou, Hsinchu (TW); Hsin-Yi Hsu, Taoyuan (TW); Li-Hsin Lin, Zhubei (TW); Yuchi Wang, New Taipei (TW); Hsin-Hsin Shen, Taipei (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 274 days.

(21) Appl. No.: 17/561,133

(22) Filed: Dec. 23, 2021

(65) Prior Publication Data
US 2022/0204772 A1 Jun. 30, 2022

Related U.S. Application Data

(60) Provisional application No. 63/131,470, filed on Dec. 29, 2020.

(51) Int. Cl.
*C08L 89/06* (2006.01)
*A61L 27/26* (2006.01)
(Continued)

(52) U.S. Cl.
CPC .............. *C08L 89/06* (2013.01); *A61L 27/26* (2013.01); *A61L 27/52* (2013.01); *B33Y 80/00* (2014.12);
(Continued)

(58) Field of Classification Search
CPC .. C08L 89/06; C08L 2203/02; C08L 2205/02; C08L 2205/16; C08L 2312/00;
(Continued)

(56) References Cited

U.S. PATENT DOCUMENTS 7,855,074 B2 12/2010 Warren et al.
2009/0208577 A1 8/2009 Xu et al.
(Continued)

FOREIGN PATENT DOCUMENTS

CN 111378149 A 7/2020
CN 111574816 A 8/2020
(Continued)

OTHER PUBLICATIONS

Antoine et al., "Review of Collagen I Hydrogels for Bioengineered Tissue Microenvironments," Tissue Engineering: Part B, vol. 20, No. 6, 2014, pp. 683-696.
(Continued)

*Primary Examiner* — Peter A Salamon
(74) *Attorney, Agent, or Firm* — Birch, Stewart, Kolasch & Birch, LLP

(57) ABSTRACT

A bioprintable material is provided. The bioprintable material includes a hydrogel and microfilaments mixed in the hydrogel. The hydrogel includes a first collagen. The microfilament includes a second collagen. The diameter of the microfilament is ranging from 5 microns to 200 microns. The weight ratio of the microfilaments to the first collagen is ranging from 0.01:1 to 10:1.

20 Claims, 6 Drawing Sheets

(51) Int. Cl.
   *A61L 27/52*   (2006.01)
   *B33Y 80/00*   (2015.01)
   *C08J 3/24*   (2006.01)
   *C12N 5/00*   (2006.01)

(52) U.S. Cl.
   CPC .............. *C08J 3/24* (2013.01); *C12N 5/0018* (2013.01); *C08J 2389/06* (2013.01); *C08J 2489/06* (2013.01); *C08L 2203/02* (2013.01); *C08L 2205/02* (2013.01); *C08L 2205/16* (2013.01); *C08L 2312/00* (2013.01); *C12N 2500/34* (2013.01)

(58) Field of Classification Search
   CPC .......... C08L 89/00; C08L 39/06; A61L 27/26; A61L 27/52; A61L 2430/00; A61L 27/48; A61L 27/24; A61L 27/16; A61L 27/18; A61L 27/20; A61L 27/222; A61L 27/58; B33Y 80/00; B33Y 10/00; B33Y 70/10; B33Y 70/00; C08J 3/24; C08J 2389/06; C08J 2489/06; C12N 5/0018; C12N 2500/34
   See application file for complete search history.

(56) References Cited

U.S. PATENT DOCUMENTS

| | | | |
|---|---|---|---|
| 2010/0196432 | A1 | 8/2010 | Feinberg et al. |
| 2015/0246072 | A1 | 9/2015 | Bhatia et al. |
| 2017/0088815 | A1 | 3/2017 | Wang et al. |
| 2018/0257297 | A1* | 9/2018 | Matheu ............... A61L 27/3625 |
| 2019/0000602 | A1* | 1/2019 | McCullen ............ D01D 5/0084 |
| 2020/0246505 | A1 | 8/2020 | Francis et al. |
| 2020/0330644 | A1* | 10/2020 | MacQueen ............ B33Y 70/00 |

FOREIGN PATENT DOCUMENTS

| | | |
|---|---|---|
| CN | 111978563 A | 11/2020 |
| TW | 201932299 A | 8/2019 |
| TW | I701364 B | 8/2020 |
| WO | WO 2020/234167 A1 | 11/2020 |

OTHER PUBLICATIONS

Diamantides et al., "Correlating rheological properties and printability of collagen bioinks: the effects of riboflavin photocrosslinking and pH," Biofabrication, vol. 9, Jul. 5, 2017, pp. 1-13.

Haynl et al., "Microfluidics-Produced Collagen Fibers Show Exraordinary Mechanical Properties," Nano Letters, vol. 16, Aug. 11, 2016, pp. 5917-5922.

Heidenreich et al., "Collagen and chitosan blends for 3D bioprinting: A rheological and printability approach," Polymer Testing, vol. 82, 2020 (Available online Dec. 18, 2019), pp. 1-9.

Hsieh et al., "Double-Network Polyurethane-Gelatin Hydrogel with Tunable Modulus for High-Resolution 3D Bioprinting," ACS Applied A rials & Interfaces, vol. 11, Aug. 13, 2019, pp. 32746-32757.

Huang, "Extrusion-based 3D Printing and Characterization of Edible Materials," Master's Thesis, University of Waterloo, 2018, pp. 1-94 (107 p. total).

Jang et al., "Tailoring mechanical properties of decellularized extracellular matrix biolink by vitamin B2-induced photocrosslinking," Acta Biomaterialia, vol. 33, 2016 (Available online Jan. 14, 2016), pp. 88-95.

Lee et al., "3D bioprinting of collagen to rebuild components of the human heart," Science, vol. 365, Issue 6452, Aug. 2, 2019, pp. 1-5.

Osidak et al., "Collagen as Bioink for Bioprinting: A Comprehensive Review," International Journal of Bioprinting, vol. 6, Issue 3, Apr. 21, 2020, pp. 1-10.

Osidak et al., "Viscoll collagen solution as a novel bioink for direct 3D bioprinting," Journal of Materials Science: Materials in Medicine, vol. 30, No. 31, 2019 (Published online Mar. 4, 2019), pp. 1-12 (13 pages total).

QI et al., "A new collagen solution with high concentration and collagen native structure perfectly preserved," RSC Advances, vol. 5, 2015 (Accepted Oct. 5, 2015), pp. 87180-87186.

Sachlos et al., "Novel collagen scaffolds with predefined internal morphology made by solid freeform fabrication," Biomaterials, vol. 24, 2003 (Accepted Oct. 15, 2002), pp. 1487-1497.

Shayegan et al., "Intact Telopeptides Enhance Interactions between Collagens," Biophysical Journal, vol. 111, Dec. 6, 2016, pp. 2404-2416.

Wu et al., "Polymers with controlled assembly and rigidity made with click-functional peptide bundles," Nature, vol. 574, Oct. 31, 2019, pp. 658-662 (15 pages total).

Zeugolis et al., "Cross-linking of extruxled collagen fibers—A biomimetic three-dimensional scaffold for tissue engineering applications," Journal of Biomedical Materials Research Part A, 2008 (Published online May 8, 2008), pp. 895-908.

Chinese Office Action for Appl. No. 202111588834.5 dated Oct. 10, 2022.

Du et al., "3D bioprinting of BMSC-laden methacrylamide gelatin scaffolds with CBD-BMP2-collagen microfibers," Biofabrication 7, Dec. 18, 2015, pp. 1-10 (11 pages total).

Extended European Search Report for European Application No. 21217493.2, dated May 23, 2022.

* cited by examiner

H = 2.5

H = 3.0

H = 3.2

BIOPRINTABLE MATERIAL AND METHOD FOR FABRICATING THE SAME

CROSS REFERENCE TO RELATED APPLICATIONS

This application claims the benefit of U.S. Provisional Application No. 63/131,470, filed on Dec. 29, 2020, the entirety of which is incorporated by reference herein.

TECHNICAL FIELD

The present disclosure relates to a bioprintable material, and more particularly to a bioprintable material mixed with collagen microfilaments.

BACKGROUND 3D-bioprinting has become a highly valued and rapidly developing technology in recent years, especially in the fields of medical treatment and tissue engineering. It can be customized to repair or regenerate damaged tissues or organs, thereby creating suitable implants for patients that can promote repair, and creating unlimited possibilities for clinical applications.

Although a variety of materials are currently used for 3D-bioprinting, it is still necessary to consider whether it has excellent biocompatibility and long-term use in other clinical applications if it involves cell scaffolds and living tissue engineering. At present, the most popular and most clinically promising material is still collagen.

Although collagen-based bio-inks have considerable advantages in biocompatibility at the practical application level, when applied to the extrusion 3D-printing process, however, their current product formulations still have many features that need to be improved. Also, the common improvement methods have their limitations.

Therefore, for the development of biomedical materials, it is still necessary to provide an improved bioprintable material.

SUMMARY

In accordance with one embodiment of the present disclosure, a bioprintable material is provided. The bioprintable material includes a hydrogel including a first collagen; and a microfilament including a second collagen mixed in the hydrogel, wherein the diameter of the microfilament is ranging from 5 μm to 200 μm, and the weight ratio of the microfilament to the first collagen is ranging from 0.01:1 to 10:1.

In some embodiments, the concentration of the first collagen in the hydrogel is ranging from 0.01 wt % to 10 wt %. In some embodiments, the first collagen includes type I collagen.

In some embodiments, the hydrogel further includes polyvinylpyrrolidone (PVP), gelatin or hydroxypropyl methylcellulose (HPMC).

In some embodiments, the weight ratio of the second collagen in the microfilament is ranging from 40% to 99%. In some embodiments, the second collagen includes type I collagen. In some embodiments, the second collagen includes telocollagen, atelocollagen or a combination thereof. In some embodiments, the microfilament further includes polyethylene glycol (PEG), polylactic acid (PLA), polycaprolactone (PCL), polyglycolide (PGA), poly(D,L-lactide-co-glycolide) (PLGA), poly(lactide-co-caprolactone) (PLCL) or a combination thereof.

In some embodiments, the length of the microfilament is ranging from 20 μm to 2 cm. In some embodiments, the length of the microfilament is ranging from 100 μm to 4 mm. In some embodiments, the ratio of the length to the diameter of the microfilament is ranging from 1 to 100. In some embodiments, the ratio of the length to the diameter of the microfilament is ranging from 3 to 50. In some embodiments, the surface of the microfilament has a microstructure. In some embodiments, the microstructure includes a plurality of straight stripes parallel to an axis, with a pitch of ranging from 1 μm to 5 μm and a depth of ranging from 0.2 μm to 4 μm. In some embodiments, the microstructure includes a plurality of horizontal stripes perpendicular to an axis, with a pitch of ranging from 0.1 μm to 50 μm. In some embodiments, the microstructure includes a plurality of protrusions or cavities with an average diameter of ranging from 10 nm to 30 μm in a cross-section.

In some embodiments, the weight ratio of the microfilament to the first collagen is ranging from 0.05:1 to 0.3:1.

In some embodiments, the bioprintable material is applied in additive bio-manufacturing, multi-microstructure gel for tissue culture, three-dimensional tissue culture material, tissue supplement dressing or tissue supplement implant.

In accordance with one embodiment of the present disclosure, a method for fabricating a bioprintable material is provided. The fabrication method includes providing a second collagen to perform a filament-forming step to form a microfilament; and mixing the microfilament and a hydrogel to produce a bioprintable material, wherein the hydrogel includes a first collagen, the diameter of the microfilament is ranging from 5 μm to 200 μm, and the weight ratio of the microfilament to the first collagen is ranging from 0.01:1 to 10:1.

In some embodiments, the method further includes performing a drying step on the microfilament after the filament-forming step.

In some embodiments, the method further includes performing a cross-linking step on the microfilament after the drying step.

In some embodiments, the method further includes performing a cutting step on the microfilament after the cross-linking step.

In the present disclosure, micron-centimeter-scale filamentous materials made of collagen are mixed into bio-inks. Under the condition that the main components of bio-ink, ion environment and collagen concentration are maintained, the characteristics such as viscosity, storage modulus, shear thinning and viscosity recovery ability of bio-ink can be greatly increased, thereby improving printability and forming accuracy. The present disclosure not only retains the advantages of collagen bio-ink, but also further improves the permeability of the material to small-molecule nutrients/ waste, provides a microstructure similar to the extracellular matrix (ECM) scale of living organisms, and increases an operable range of structure degradation rate. The modification strategy of this bio-ink not only improves the common defects of collagen bio-ink in 3D bioprinting applications, but also makes it more widely used in cell-tissue culture matrix and carrier, surgical wound fillings and other tissue engineering applications.

A detailed description is given in the following embodiments with reference to the accompanying drawings.

DETAILED DESCRIPTION

Figure 1:
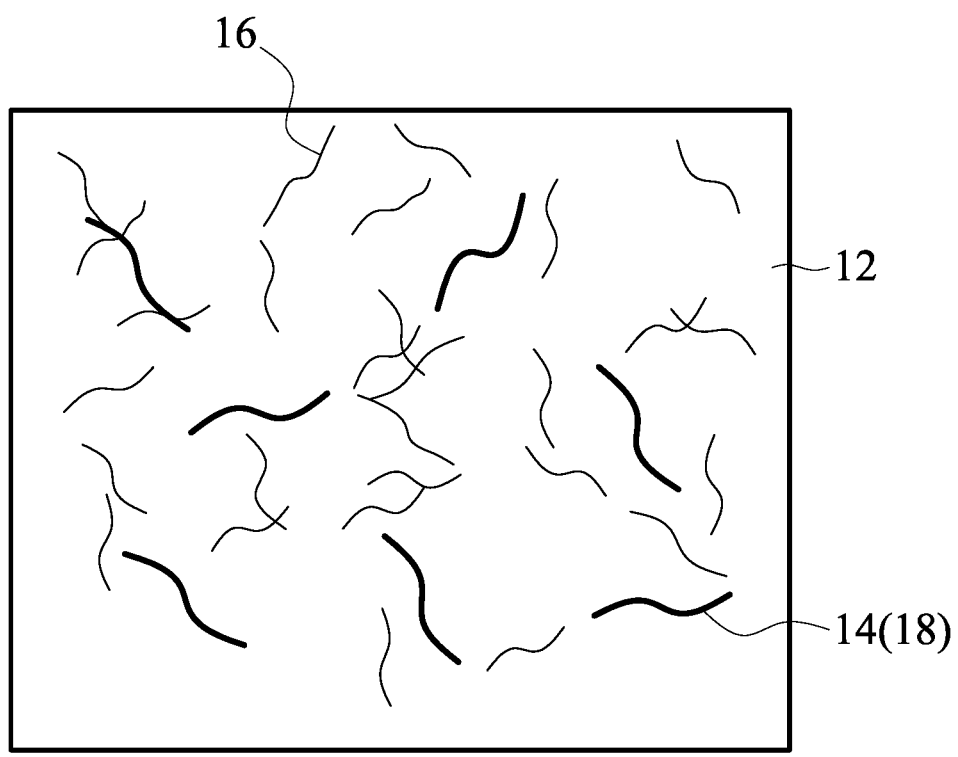
FIG. 1 is a schematic diagram of a bioprintable material in accordance with one embodiment of the present disclosure.

In accordance with one embodiment of the present disclosure, a bioprintable material 10 is provided. FIG. 1 is a schematic diagram of the bioprintable material 10.

As shown in FIG. 1, the bioprintable material 10 includes a hydrogel 12 and microfilaments 14. The microfilaments 14 are mixed in the hydrogel 12. The hydrogel 12 includes a first collagen 16. The microfilament 14 includes a second collagen 18. The diameter of the microfilament 14 is ranging from about 5 μm to about 200 μm, for example, from about 5 μm to about 190 μm, from about 10 μm to about 180 μm, from about 20 μm to about 150 μm, from about 30 μm to about 160 μm, from about 50 μm to about 125 μm, about 15 μm, about 35 μm, about 55 μm, about 75 μm, about 95 μm, about 100 μm, about 115 μm, about 135 μm, about 160 μm, about 175 μm, about 185 μm, etc., but the present disclosure is not limited thereto. The weight ratio of the microfilament 14 to the first collagen 16 is ranging from about 0.01:1 to about 10:1, for example, from about 0.02:1 to about 10:1, from about 0.05:1 to about 9:1, from about 0.08:1 to about 8:1, from about 0.1:1 to about 7:1, from about 0.2:1 to about 6:1, from about 0.5:1 to about 5:1, from about 0.8:1 to about 5:1, from about 0.9:1 to about 4.5:1, about 0.25:1, about 0.75:1, about 1:1, about 2:1, about 3:1, about 7.5:1, etc., but the present disclosure is not limited thereto.

In some embodiments, the concentration of the first collagen 16 in the hydrogel 12 is ranging from about 0.01 wt % to about 10 wt %, for example, from about 0.02 wt % to about 10 wt %, from about 0.05 wt % to about 10 wt %, from about 0.1 wt % to about 8 wt %, from about 0.2 wt % to about 8 wt %, from about 0.3 wt % to about 8 wt %, from about 0.5 wt % to about 7.5 wt %, from about 0.8 wt % to about 7 wt %, from about 1 wt % to about 5 wt %, about 0.75 wt %, about 1.25 wt %, about 2.5 wt %, about 7.5 wt %, etc., but the present disclosure is not limited thereto. In one embodiment, the concentration of the first collagen 16 in the hydrogel 12 is ranging from about 0.4 wt % to about 2.5 wt %. In one embodiment, the concentration of the first collagen 16 in the hydrogel 12 is ranging from about 0.7 wt % to about 2.5 wt %. In some embodiments, the first collagen 16 includes type I collagen.

In some embodiments, the hydrogel 12 further includes polyvinylpyrrolidone (PVP), gelatin or hydroxypropyl methylcellulose (HPMC).

In some embodiments, the weight ratio of the second collagen 18 in the microfilament 14 is ranging from about 40% to about 99%, for example, from about 45% to about 95%, from about 50% to about 90%, from about 55% to about 85%, from about 60% to about 80%, about 42%, about 48%, about 53%, about 57%, about 62%, about 65%, about 72%, about 75%, about 83%, about 88%, about 92%, about 97%, etc., but the present disclosure is not limited thereto. In some embodiments, the second collagen 18 includes type I collagen. In some embodiments, the second collagen 18 includes telocollagen, atelocollagen or a combination thereof. In some embodiments, the microfilament 14 further includes polyethylene glycol (PEG), polylactic acid (PLA), polycaprolactone (PCL), polyglycolide (PGA), poly(D,L-lactide-co-glycolide) (PLGA), poly(lactide-co-caprolactone) (PLCL) or a combination thereof, but the present disclosure is not limited thereto. Other biodegradable polymers are also suitable for use in the present disclosure.

In some embodiments, the diameter of the microfilament 14 is ranging from about 5 μm to about 200 μm, for example, from about 5 μm to about 180 μm, from about 5 μm to about 160 μm, from about 5 μm to about 140 μm, from about 5 μm to about 120 μm, from about 5 μm to about 100 μm, from about 5 μm to about 80 μm, from about 5 μm to about 50 μm, about 10 μm, about 20 μm, about 30 μm, about 40 μm, about 50 μm, etc., but the present disclosure is not limited thereto.

In some embodiments, the length of the microfilament 14 is ranging from about 100 μm to about 4 mm, for example, from about 150 μm to about 3.8 mm, from about 200 μm to about 3.6 mm, from about 200 μm to about 2.4 mm, from about 200 μm to about 1.2 mm, from about 200 μm to about 1 mm, from about 300 μm to about 3.5 mm, from about 500 μm to about 3.2 mm, from about 800 μm to about 3 mm, from about 200 μm to about 500 μm, from about 100 μm to about 1.4 mm, from about 600 μm to about 1.2 mm, about 250 μm, about 350 μm, about 450 μm, about 750 μm, about 880 μm, about 1 mm, about 1.5 mm, about 1.8 mm, about 2 mm, about 2.5 mm, etc., but the present disclosure is not limited thereto.

In some embodiments, the ratio of the length to the diameter of the microfilament 14 is ranging from about 1 to about 100, for example, from about 2 to about 98, from about 3 to about 95, from about 5 to about 92, from about 8 to about 90, from about 12 to about 96, from about 15 to about 90, about 20, about 30, about 40, about 50, etc., but the present disclosure is not limited thereto. In some embodiments, the ratio of the length to the diameter of the microfilament 14 is ranging from about 3 to about 50.

In some embodiments, the surface of the microfilament 14 may have a microstructure. In some embodiments, the microstructure on the surface of the microfilament 14 may include a parallel-arranged configuration. If nerve cells are cultured in it, favorable nerve conduction pathways will be formed. In some embodiments, the microstructure on the surface of the microfilament 14 may include a plurality of straight stripes parallel to an axis, with a pitch of ranging from about 1 μm to about 5 μm and a depth of ranging from about 0.2 μm to about 4 μm. The aforementioned pitch may be, for example, about 1.2 μm, about 1.3 μm, about 1.5 μm, about 1.8 μm, etc., but the present disclosure is not limited thereto. The aforementioned depth may be, for example, about 0.3 μm, about 0.5 μm, about 0.8 μm, about 1 μm, about 1.2 μm, about 1.5 μm, about 1.8 μm, about 2 μm, about 2.2 μm, about 2.5 μm, about 3 μm, about 3.3 μm, about 3.7 μm, etc., but the present disclosure is not limited thereto. In some embodiments, the microstructure on the surface of the microfilament 14 may include a plurality of horizontal stripes perpendicular to an axis, with a pitch of ranging from about 0.1 μm to about 50 μm, for example, from about 0.5 μm to about 50 μm, from about 1 μm to about 50 μm, from about 1.5 μm to about 45 μm, from about 2 μm to about 42 μm, from about 3 μm to about 45 μm, from about 5 μm to about 40 μm, from about 6 μm to about 36 μm, about 8 μm, about 10 μm, about 15 μm, about 20 μm, about 27 μm, about 32 µm, about 48 µm, etc., but the present disclosure is not limited thereto. In some embodiments, the microstructure on the surface of the microfilament 14 includes a plurality of protrusions or cavities with an average diameter of ranging from about 10 nm to about 30 µm in a cross-section, for example, from about 20 nm to about 30 µm, from about 30 nm to about 25 µm, from about 50 nm to about 20 µm, from about 100 nm to about 22 µm, from about 200 nm to about 18 µm, from about 500 nm to about 15 µm, from about 800 nm to about 12 µm, about 75 nm, about 150 nm, about 300 nm, about 750 nm, about 1 µm, about 1.5 µm, about 2 µm, about 2.5 µm, about 3.2 µm, about 4.8 µm, about 5.5 µm, about 6 µm, about 7.5 µm, about 8 µm, about 10 µm, etc., but the present disclosure is not limited thereto.

In some embodiments, the weight ratio of the microfilament 14 to the first collagen 16 is ranging from about 0.05:1 to about 0.3:1, for example, about 0.07:1, about 0.08:1, about 0.1:1, about 0.15:1, about 0.2:1 or about 0.25:1, but the present disclosure is not limited thereto.

In some embodiments, the bioprintable material 10 may be applied in additive bio-manufacturing, multi-microstructure gel for tissue culture, three-dimensional tissue culture material, tissue supplement dressing or tissue supplement implant, etc., but the present disclosure is not limited thereto. In some embodiments, the bioprintable material 10 may be used for tissue-engineering research models, tissue culture for transplantation, wound repair or supplement dressing for aesthetic medicine, etc., but the present disclosure is not limited thereto.

In accordance with one embodiment of the present disclosure, a method for fabricating a bioprintable material is provided. First, a second collagen is provided to proceed to a filament-forming step to form a microfilament. Next, the microfilament and a hydrogel are mixed to fabricate a bioprintable material, as shown in FIG. 1. The bioprintable material 10 includes the hydrogel 12 and the microfilaments 14. The microfilaments 14 are mixed in the hydrogel 12. The hydrogel 12 includes a first collagen 16. The microfilament 14 includes the second collagen 18. The diameter of the microfilament 14 is ranging from about 5 µm to about 200 µm. The weight ratio of the microfilament 14 to the first collagen 16 is ranging from about 0.01:1 to about 10:1.

The diameter range of the microfilament 14 and the weight ratio range of the microfilament 14 to the first collagen 16 are approximately the same as the applicable range of the bioprintable material in the above embodiment. For details, please refer to the above content, and there is no repeat here.

In some embodiments, the fabrication method further includes performing a drying step on the microfilament after the filament-forming step, wherein the drying manners may include, but are not limited to, room-temperature drying, thermal-convection drying or air-blowing drying.

In some embodiments, the fabrication method further includes performing a cross-linking step on the microfilament after the drying step, wherein the cross-linking manners may include, but are not limited to, chemical crosslinking, photo crosslinking or thermal crosslinking.

In some embodiments, the fabrication method further includes performing a cutting step on the microfilament after the cross-linking step, wherein the cutting manners may include, but are not limited to, knife-mold cutting, automatic-cutting-tool cutting or manual cutting.

In some embodiments, the fabrication method of the microfilament 14 includes the use of wet spinning with a coaxial needle to fabricate the microfilament. The use of the coaxial needle is to provide a collagen solution and a filament-forming solution in contact in a stable flow field to maintain the stability of the filamentous state. The tiny coaxial needle used in the present disclosure can produce collagen fibers (microfilaments) with a diameter of approximately 50 µm. The outer needle of the coaxial needle needs to be longer than the inner needle to create a space for stable liquid contact. An aqueous solution with high acid-base buffering capacity is used as a sheath flow. The viscosity of the aqueous solution is adjusted by polymer. An acidic collagen aqueous solution is used as a core solution. The appropriate flow rate is adjusted, and an injection pump is used to simultaneously squeeze the two material solutions into water, an acid-base buffer solution or a background solution of an organic solution to initially form filaments. The present disclosure uses, for example, alcohols as the background solution for filament formation, which can accelerate fiber dehydration and aggregation and simplify subsequent processing procedures. After the initial filament formation, it is continuously rolled up and collected by a spool. In order to avoid stacking and sticking of material solutions, the present disclosure uses a slope structure to disperse the outflowing liquid. Other methods such as specific gravity liquids can also be used to avoid the above-mentioned problem of stacking and sticking of material solutions.

In some embodiments, the fabrication method of the microfilament 14 may also include electrospinning or microchannel manufacturing, but the present disclosure is not limited thereto.

In some embodiments, the electrospinning includes the following steps: (1) an electro-spinning solution is placed in a syringe, and electrodes are connected to a needle end, (2) the current and voltage are adjusted to stably spray the solution on a carrier or roller, and (3) after drying, electrospinning filament is obtained and further crosslinked according to the needs of use.

In some embodiments, the micro-channel manufacturing includes the following steps: (1) a micro-sculpture plastic substrate is laminated, (2) silicone MEMS transfer printing is performed, and (3) a coaxial needle is used (i.e. a composite needle with an inner needle contained in an exit section of an outer needle).

In some embodiments, in order to stabilize fiber so that it will not continue to swell or disintegrate in a colloidal solution, a certain degree of stabilization process is required for the fiber. The present disclosure uses a cross-linking agent, such as aldehyde gas or 1-ethyl-3-(3-dimethylaminopropyl)-carbodiimide (EDC)/N—N-hydroxysuccinimide (NHS), to permeate the fiber, so that protein molecules are crosslinked and fixed to an appropriate degree (this is chemical crosslinking). In some embodiments, other cross-linking manners such as thermal crosslinking or photo crosslinking may also be used to crosslink and fix the fiber. In some embodiments, the thermal crosslinking may include placing microfilaments in an oven and stable heating at 60-100° C. for a period of time after drying. For example, heating for about 1 minute to about 24 hours, about 10 minutes to about 18 hours, about 30 minutes to about 12 hours, about 1 hour, about 2 hours, about 3 hours, about 6 hours, etc., but the present disclosure is not limited thereto. In some embodiments, the photo crosslinking may include placing the microfilament fiber under an ultraviolet-light source and irradiating with a light wavelength of 100 nm to 400 nm for about 1 minute to about 5 hours after drying. For example, irradiating for about 5 minutes to about 3 hours, about 10 minutes, about 30 minutes, about 45 minutes, about 1 hour, about 2 hours, about 4 hours, etc., but the present disclosure is not limited thereto.

In some embodiments, the mixing manner of fiber and colloid includes the mixing of the colloid and fiber-containing diluent (this is the syringe mixing manner). Since general heterogeneous mixing is prone to inhomogeneous phenomena such as precipitation, in the present disclosure, a colloidal solution first stays in a low-temperature ungelled state for one day. Next, in the colloid, samples are taken along different positions in sequence along the direction of the gravitational field, and the weight after drying is measured to confirm the distribution of solids. The time for uniformly suspending fibers in the disclosed colloidal solution may reach 3 hours to several days without rapid sedimentation to affect the use. In some embodiments, other mixing manners may also be used, such as mixing with a colloid-mixing nozzle, mixing with a coaxial needle, or mixing with stirring, etc. In some embodiments, the mixing with a colloid-mixing nozzle includes extruding the fiber-containing diluent and the collagen colloid into the colloid-mixing nozzle, and the two are dispersed into a uniform colloid by a spoiler structure inside the needle. This step can be implemented in layered printing applications or when preparing the mixed colloid. In some embodiments, the mixing with a coaxial needle includes extruding the fiber-containing diluent and the collagen colloid from different positions of the coaxial needle, so that the two are dispersed into a colloid. In general, the collagen colloid is placed in the outer needle, but it is not limited to this configuration. This step can be implemented in layered printing applications or when preparing the mixed colloid. In some embodiments, the mixing with stirring includes adding the fiber-containing diluent and the collagen colloid to the same container, and mixing by physical means like fan blades/stirring bars, etc., in an environment that is kept below the gelation temperature. This step can be implemented in colloid preparation.

In the present disclosure, micron-centimeter-scale filamentous materials made of collagen are mixed into bio-inks. Under the condition that the main components of bio-ink, ion environment and collagen concentration are maintained, the characteristics such as viscosity, storage modulus, shear thinning and viscosity recovery ability of bio-ink can be greatly increased, thereby improving printability and forming accuracy. The present disclosure not only retains the advantages of collagen bio-ink, but also further improves the permeability of the material to small-molecule nutrients/waste, provides a microstructure similar to the extracellular matrix (ECM) scale of living organisms, and increases an operable range of structure degradation rate. The modification strategy of this bio-ink not only improves the common defects of collagen bio-ink in 3D bioprinting applications, but also makes it more widely used in cell-tissue culture matrix and carrier, surgical wound fillings and other tissue engineering applications.

Preparation Example 1

Preparation of Fiber-Colloid Mixture (1) Use of a coaxial needle: The inner needle contained collagen. The outer needle contained polymer solution. The length of the outer needle used was greater than the length of the inner needle by at least 0.5 cm. The length of the inner needle was greater than 1 cm. The end of the inner needle had a narrow chamfer (that is, the thickness of the needle wall at the exit was gradually decreased).

(2) Collagen into filaments: In this preparation example, the coaxial needle was used to provide the collagen liquid and the filament-forming solution in contact in a stable flow field to form filaments. An aqueous solution with high acid-base buffering capacity and adjustable viscosity was a sheath flow flowing in the outer needle. An acidic collagen aqueous solution was a core solution in the inner needle. The appropriate flow rate was adjusted, and an injection pump was used to simultaneously squeeze the two material solutions into water, an acid-base buffer solution or a dehydration solution of an organic solution to initially form filaments. After the initial filament formation, it is continuously rolled up and collected by a spool to prevent it from sticking.

(3) Drying of fiber: The fiber was hung at room temperature to increase air convection and promote fiber drying.

(4) Crosslinking of fiber: Chemical crosslinking, photo crosslinking or thermal crosslinking can be used. The chemical crosslinking was, for example, exposing the fiber to diluted aldehyde chemicals in gas or liquid phase for 10 minutes to several hours. The photo crosslinking was, for example, placing the dried microfilament fiber under an ultraviolet-light source and irradiating it with a certain wavelength and dose for a certain period of time. The thermal crosslinking was, for example, placing the dried microfilament in an oven and heating it stably at 60-100° C. for 1 minute to 24 hours.

(5) Cutting of fiber: A knife mold or other automatic cutting tools was used to cut the fiber to the required length in the drying state, for example, cutting to 100 μm to 4 mm.

(6) Mixing of fiber and colloid: In this preparation example, the syringe mixing was used. That is, the fiber-containing diluent and the collagen colloid were placed in two syringes respectively. The syringes were assembled with a joint connector. The mixing process was completed after pushing and mixing.

| Colloidal sample table | | | | | | | | | | | | | |
|---|---|---|---|---|---|---|---|---|---|---|---|---|---|
| Colloid number | 1 | 2 | 3 | 4 | 5 | 6 | 7 | 8 | 9 | 10 | 11 | 12 | 13 |
| Collagen (%) | 1.44 | 1.44 | 1.8 | 1.2 | 1.2 | 1.2 | 1.2 | 0.44 | 0.44 | 0.96 | 0.96 | 1.2 | 1.2 |
| Fiber (%) | 0 | 20 | 20 | 0 | 0.2 | 0 | 0.48 | 0 | 0.3 | 0 | 0.3 | 0 | 0.24 |

Example 1

Dispersion Stability Test

In this example, the mixture of fiber and colloid was placed in a low-temperature syringe in a non-gelled state for one day. The colloid was sampled along different positions in sequence along the direction of the gravitational field. The weight after drying was measured to confirm the distribution of solids.

In this example, the dispersion stability test was performed on colloidal sample 1 (containing 1.44% collagen), colloidal sample 2 (containing 1.44% collagen and 20% fiber), and colloidal sample 3 (containing 1.8% collagen and 20% fiber). Each sample was placed in a syringe and kept cold for 24 hours. Next, the colloid was extruded at different stages (five sampling points in total). The variation of the proportion of solids (dry weight) in the colloid was measured. The results are shown in FIG. 2.

Figure 2:
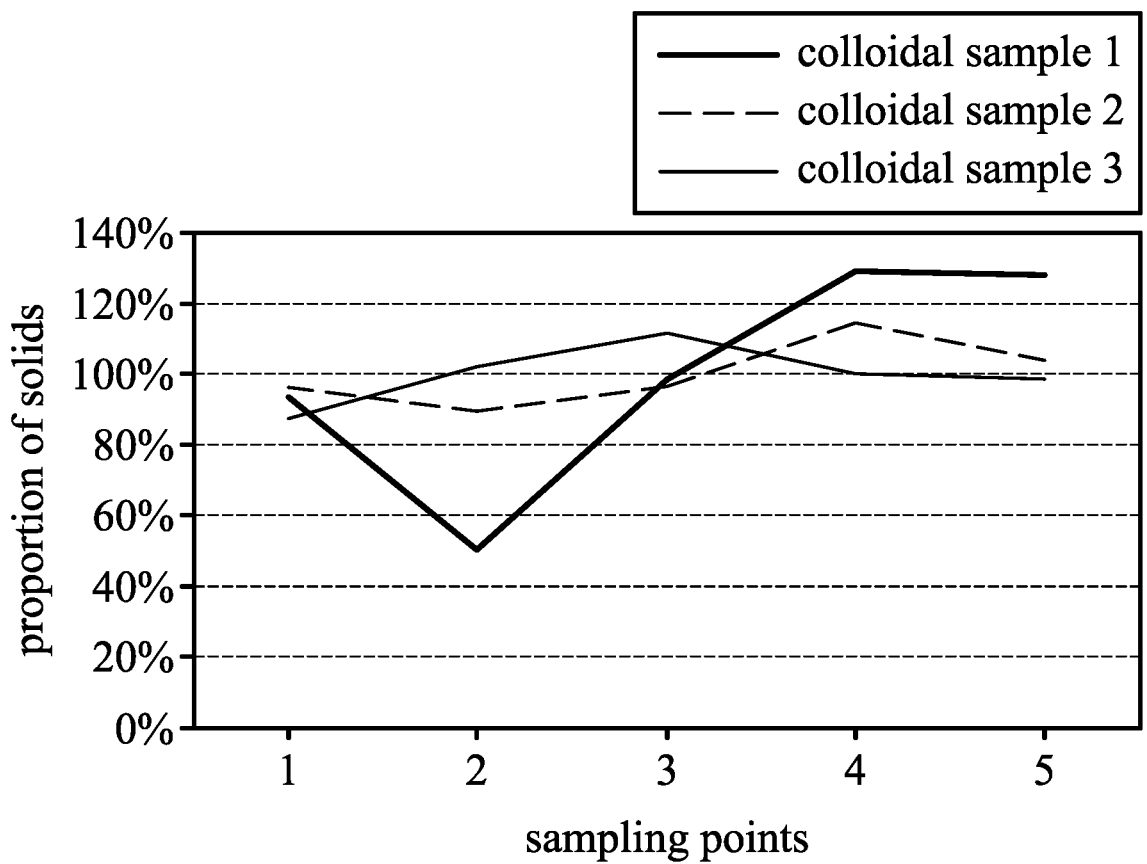
FIG. 2 shows dispersion stability of each colloidal sample in accordance with one embodiment of the present disclosure.

It can be seen from the results in FIG. 2 that the colloidal sample 1 presented a state of uneven mixing (the proportion of solids changed significantly at different stages), while the colloidal samples 2 and 3 presented a uniformly mixed state (the proportion of solids did not change significantly at different stages). It can be verified that the environment of viscosity and specific gravity provided by the colloidal solution of the present disclosure will not cause the fiber to settle rapidly in the colloidal solution and affect the use.

Example 2

Extrusion Test

In this example, the extrusion test was performed on colloidal sample 4 (containing 1.2% collagen) and colloidal sample 5 (containing 1.2% collagen and 0.2% fiber). A dynamic rheometer was used. The colloid stayed at 4° C. to equilibrate for 15 minutes in advance. The time required for the storage modulus (G') to exceed the loss modulus (G") after heating to 37° C. was measured (1 Hz/1% oscillation measurement). The results are shown in FIG. 3.

Figure 3:
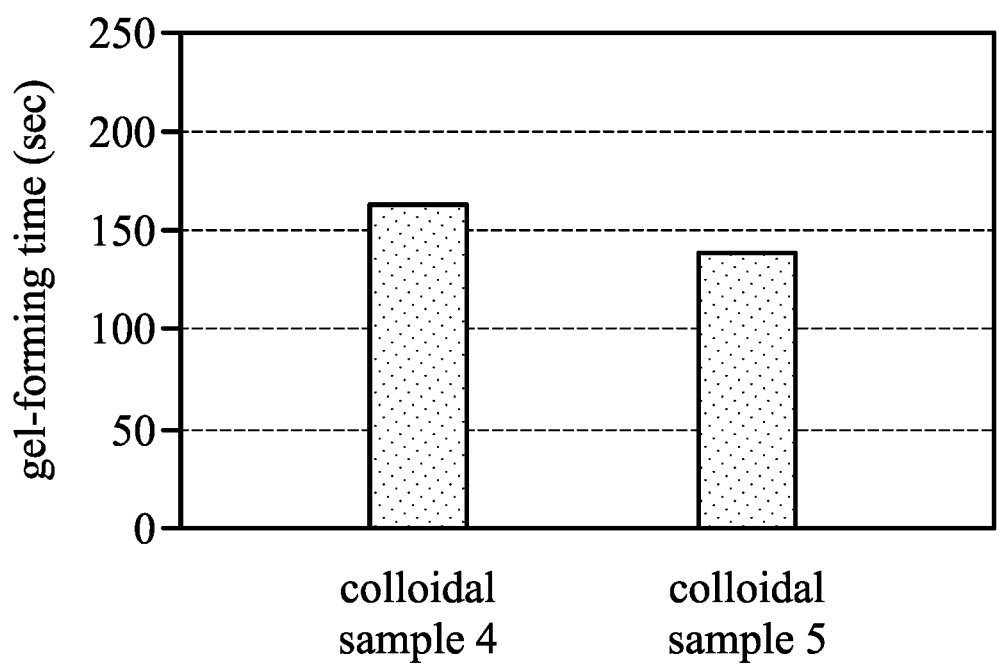
FIG. 3 shows gelation time of each colloidal sample in accordance with one embodiment of the present disclosure.

It can be seen from the results in FIG. 3 that, compared with the colloidal sample 4, the colloidal sample 5 reduced the gelation time by about 15%. After extrusion, the colloidal sample 5 had better ability of continuous stacking, and produced a higher continuous printing stack than the colloidal sample 4 (the height of continuous stacking of the colloidal sample 4 was less than 3 mm, however, the height of continuous stacking of the colloidal sample 5 was greater than 5 mm, and even reached more than 10 mm).

Example 3

Shape Self-Maintaining Test

The purpose of this example is to test the strengthening effect of fibers in larger-scale colloids.

Mold: a lipstick glue container (inner diameter: 1.4 cm, inner height: 4.4 cm); an inner screw (diameter: 0.4 cm, height: 3.5 cm).

Gel formation: 6 ml of colloid was loaded into the mold, packaged in a plastic bag, and heated in a water bath at 37° C. for 30 minutes.

Material composition: colloidal sample 6 (containing 1.2% collagen); colloidal sample 7 (containing 1.2% collagen and 0.48% fiber).

Measurement: the colloid was slowly rolled out (no vibration), and the height was recorded.

Figure 4A:
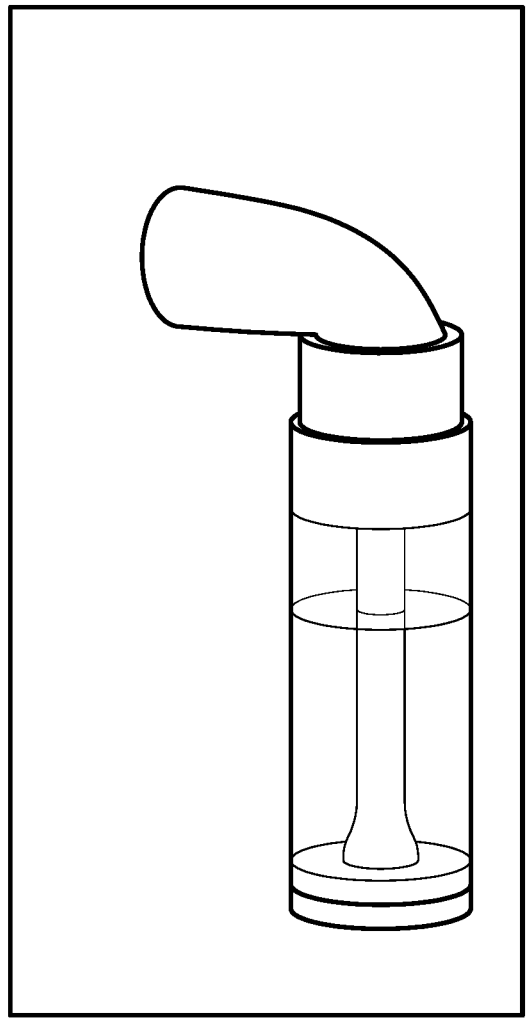
FIG. 4A is a shape self-maintaining test of a colloidal sample without fiber in accordance with one embodiment of the present disclosure.
Figure 4B:
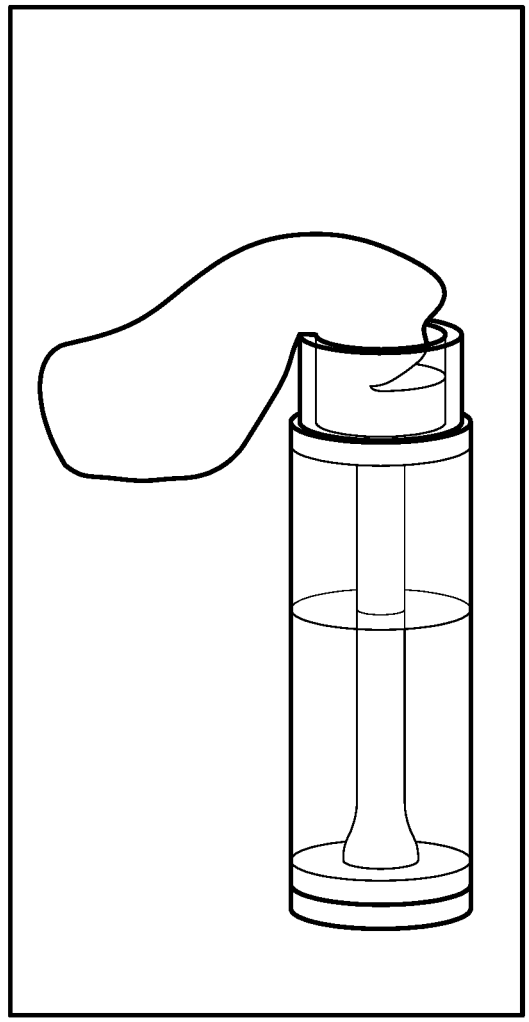
FIG. 4B is a shape self-maintaining test of a colloidal sample without fiber in accordance with one embodiment of the present disclosure.
Figure 4C:
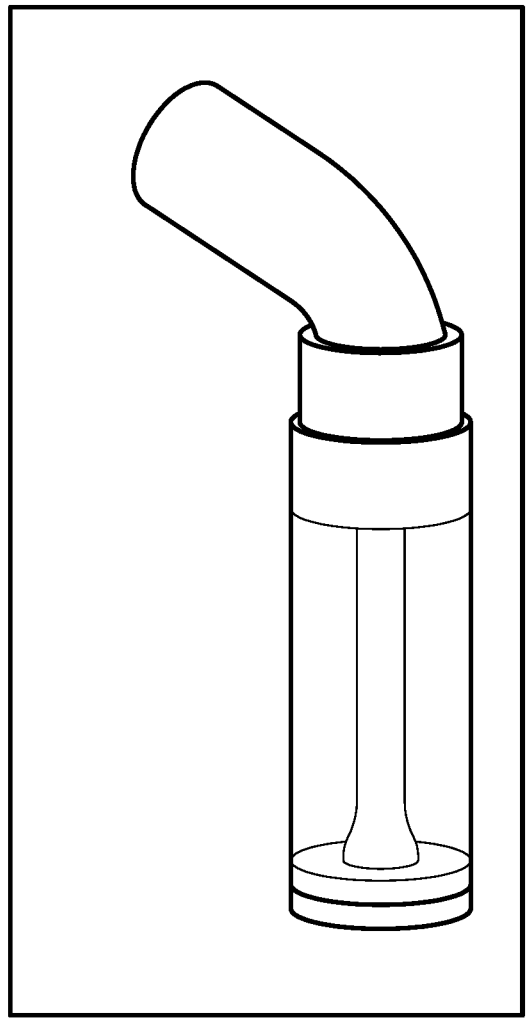
FIG. 4C is a shape self-maintaining test of a fiber-containing colloidal sample in accordance with one embodiment of the present disclosure.

Test results: the support height (the center of gravity can be stably maintained in the projection of the bottom surface) of the colloidal sample 6 was about 2.5 cm (as shown in FIG. 4A). When the support height was increased to 3.0 cm, the colloid was broken due to severe bending (as shown in FIG. 4B). The support height of the colloidal sample 7 was about 3.2 cm (as shown in FIG. 4C). Obviously, the colloidal sample 7 can tolerate a higher colloid height without serious bending or even breaking.

Strengthening effect: the support height of the colloidal sample 7 was about 0.7 cm higher than that of the colloidal sample 6 (the self-supporting capacity was increased by more than 28%).

Example 4

Storage Modulus Test (the Initial Storage Modulus at 37° C.)

In this example, the storage modulus test (the initial storage modulus at 37° C.) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). A dynamic rheometer was used. The colloid stayed at 4° C. to equilibrate for 15 minutes in advance. The initial storage modulus (G') after heating to 37° C. was measured (1 Hz/1% oscillation measurement). The results are shown in Table 1.

TABLE 1

| Colloidal samples | 9 | 11 | 13 |
|---|---|---|---|
| Storage modulus (Pa) | +0.04 | +0.38 | +1.15 |
| Compared with the samples without fiber | +56.5% | +4.2% | +11.9% |

From the test results in Table 1, it can be verified that, regardless of the colloidal samples 8, 10 and 12 (no fiber added), after adding fibers (such as the colloidal samples 9, 11 and 13), their storage modulus in the gelation step can be increased.

Example 5

Storage Modulus Test (the Storage Modulus after Ten Minutes of Gelation)

In this example, the storage modulus test (the storage modulus after ten minutes of gelation) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). A dynamic rheometer was used. The colloid stayed at 4° C. to equilibrate for 15 minutes in advance. The storage modulus (G') after heating to 37° C. for ten minutes was measured (1 Hz/1% oscillation measurement). The results are shown in Table 2.

TABLE 2

| Colloidal samples | 9 | 11 | 13 |
|---|---|---|---|
| Storage modulus (Pa) | +0.05 | +0.30 | +2.95 |
| Compared with the samples without fiber | +48.8% | +3.9% | +41.6% |

From the test results in Table 2, it can be verified that, regardless of the colloidal samples 8, 10 and 12 (no fiber added), after adding fibers (such as the colloidal samples 9, 11 and 13), the storage modulus after gelation can be increased.

Example 6

Viscosity Test (the Viscosity at the Beginning of Deceleration after High-Speed Shearing)

In this example, the viscosity test (the viscosity at the beginning of deceleration after high-speed shearing) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). A dynamic rheometer was used to measure. In flow mode, the speed of 0.15 s$^{-1}$, 100 s$^{-1}$ and 0.15 s$^{-1}$ was set for one minute each. The dynamic viscosity was measured during the period. The results are shown in Table 3.

TABLE 3

| Colloidal samples | 9 | 11 | 13 |
|---|---|---|---|
| Viscosity (cP) | −173.7 | +5314.8 | +881.6 |
| Compared with the samples without fiber | −52.7% | +30.8% | +5.5% |

From the test results in Table 3, it can be verified that, regardless of the colloidal samples 10 and 12 (no fiber added), after adding fibers (such as the colloidal samples 11 and 13), the viscosity at the beginning of deceleration after high-speed shearing can be increased.

Example 7

Pressure Test (the Compressive Elastic Coefficient at 1% Deformation)

In this example, the pressure test (the compressive elastic coefficient at 1% deformation) by rapid compression (the compression speed was 0.5 to 0.67%/s) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). A dynamic rheometer was used. The colloid stayed at 4° C. to equilibrate for 15 minutes in advance. After heating to 37° C. for thirty minutes, a positive force was applied to compress at the above compression speed. The variation of the contact force was measured and further converted into a coefficient of elasticity. The results are shown in Table 4.

TABLE 4

| Colloidal samples | 9 | 11 | 13 |
|---|---|---|---|
| Coefficient of elasticity (kPa) | +2.8 | +85.731 | −1.897 |
| Compared with the samples without fiber | +12.1% | +19.7% | −0.73% |

From the test results in Table 4, it can be verified that, regardless of the colloidal samples 8 and 10 (no fiber added), after adding fibers (such as the colloidal samples 9 and 11), even under high-impact compression conditions, the elasticity can also be increased.

Example 8

Pressure Test (the Maximum Pressure that can be Withstood Before the First Stage of Deformation)

In this example, the pressure test (the maximum pressure that can be withstood before the first stage of deformation) by rapid compression (the compression speed was 0.5 to 0.67%/s) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). The experimental procedure is the same as in Example 7. The first maximum pressure peak was recorded. The results are shown in Table 5.

TABLE 5

| Colloidal samples | 9 | 11 | 13 |
|---|---|---|---|
| Pressure (kPa) | +0.20 | +0.39 | −0.68 |
| Compared with the samples without fiber | +72.8% | +8.0% | −13.7% |

From the test results in Table 5, it can be verified that, regardless of the colloidal samples 8 and 10 (no fiber added), after adding fibers (such as the colloidal samples 9 and 11), even under high-impact compression conditions, the pressure resistance can also be improved.

Example 9

Pressure Test (the Compressive Elastic Coefficient at 0.5% Deformation)

In this example, the pressure test (the compressive elastic coefficient at 0.5% deformation) by slow compression (the compression speed was 0.033%/s) was performed on colloidal sample 8 (containing 0.44% collagen), colloidal sample 9 (containing 0.44% collagen and 0.3% fiber), colloidal sample 10 (containing 0.96% collagen), colloidal sample 11 (containing 0.96% collagen and 0.3% fiber), colloidal sample 12 (containing 1.2% collagen) and colloidal sample 13 (containing 1.2% collagen and 0.24% fiber). The experimental procedure is the same as in Example 7. The first maximum pressure peak was recorded. The compressive elastic coefficient at 0.5% deformation was recorded. The results are shown in Table 6.

TABLE 6

| Colloidal samples | 9 | 11 | 13 |
|---|---|---|---|
| Coefficient of elasticity (kPa) | −7.08 | +15.4 | +3.17 |
| Compared with the samples without fiber | −62.5% | +8.8% | +4.7% |

From the test results in Table 6, it can be verified that, regardless of the colloidal samples 10 and 12 (no fiber added), after adding fibers (such as the colloidal samples 11 and 13), under extremely slow compression conditions, the elasticity can be increased.

Example 10

Cell Culture Test

In this example, the cell culture test was performed on colloidal sample 4 (containing 0.96% collagen and 0.3% fiber) and colloidal sample 5 (containing 1.2% collagen). The cells used in the cell culture test were human fibroblast and human keratinocyte. Both were inoculated on the above colloidal samples at a cell concentration of 1×10$^5$ cell/ml, and cultured in a cell incubator with constant temperature of 37° C. and constant humidity.

Test results: during the culture period, the samples were taken out every 2-3 days to observe the cell type and growth condition under a microscope. H&E stained sections were performed on the 16th day after culture. The results of sectioning showed that both fibroblasts and keratinocytes grew well in the above-mentioned colloids, indicating that the bioprintable material provided by the present disclosure has good cytocompatibility.

While the invention has been described by way of example and in terms of the preferred embodiments, it should be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A bioprintable material, comprising:
   a hydrogel comprising a first collagen; and
   a microfilament comprising a second collagen mixed in the hydrogel, wherein the microfilament has a diameter of ranging from 5 μm to 200 μm, and the microfilament and the first collagen have a weight ratio of ranging from 0.01:1 to 10:1.

2. The bioprintable material as claimed in claim 1, wherein the first collagen in the hydrogel has a concentration of ranging from 0.01 wt % to 10 wt %.

3. The bioprintable material as claimed in claim 2, wherein the first collagen comprises type I collagen.

4. The bioprintable material as claimed in claim 1, wherein the hydrogel further comprises polyvinylpyrrolidone (PVP), gelatin or hydroxypropyl methylcellulose (HPMC).

5. The bioprintable material as claimed in claim 1, wherein the second collagen in the microfilament has a weight ratio of ranging from 40% to 99%.

6. The bioprintable material as claimed in claim 5, wherein the second collagen comprises type I collagen.

7. The bioprintable material as claimed in claim 6, wherein the second collagen comprises telocollagen, atelocollagen or a combination thereof.

8. The bioprintable material as claimed in claim 1, wherein the microfilament further comprises polyethylene glycol (PEG), polylactic acid (PLA), polycaprolactone (PCL), polyglycolide (PGA), poly(D,L-lactide-co-glycolide) (PLGA), poly(lactide-co-caprolactone) (PLCL) or a combination thereof.

9. The bioprintable material as claimed in claim 1, wherein the diameter of the microfilament is ranging from 5 μm to 50 μm.

10. The bioprintable material as claimed in claim 9, wherein the microfilament has a length of ranging from 20 μm to 2 cm.

11. The bioprintable material as claimed in claim 10, wherein a ratio of the length to the diameter of the microfilament is ranging from 1 to 100.

12. The bioprintable material as claimed in claim 1, wherein the microfilament has a surface with a microstructure.

13. The bioprintable material as claimed in claim 12, wherein the microstructure comprises a plurality of straight stripes parallel to an axis with a pitch of ranging from 1 μm to 5 μm and a depth of ranging from 0.2 μm to 4 μm.

14. The bioprintable material as claimed in claim 12, wherein the microstructure comprises a plurality of horizontal stripes perpendicular to an axis with a pitch of ranging from 0.1 μm to 50 μm.

15. The bioprintable material as claimed in claim 12, wherein the microstructure comprises a plurality of protrusions or cavities with an average diameter of ranging from 10 nm to 30 μm in a cross-section.

16. The bioprintable material as claimed in claim 1, wherein the weight ratio of the microfilament to the first collagen is ranging from 0.05:1 to 0.3:1.

17. A method for fabricating a bioprintable material, comprising:
    providing a second collagen to perform a filament-forming step to form a microfilament; and
    mixing the microfilament and a hydrogel to produce a bioprintable material, wherein the hydrogel comprises a first collagen, the microfilament has a diameter of ranging from 5 μm to 200 μm, and the microfilament and the first collagen have a weight ratio of ranging from 0.01:1 to 10:1.

18. The method for fabricating a bioprintable material as claimed in claim 17, further comprising performing a drying step on the microfilament after the filament-forming step.

19. The method for fabricating a bioprintable material as claimed in claim 18, further comprising performing a cross-linking step on the microfilament after the drying step.

20. The method for fabricating a bioprintable material as claimed in claim 19, further comprising performing a cutting step on the microfilament after the cross-linking step.

* * * * *